(12) United States Patent
Guillen Portal (10) Patent No.: US 11,632,923 B2
(45) Date of Patent: Apr. 25, 2023

(54) *CAMELINA SATIVA* VARIETY "SO-100"

(71) Applicant: Sustainable Oils, Inc., Torrance, CA (US)

(72) Inventor: Fernando Guillen Portal, College Station, TX (US)

(73) Assignee: SUSTAINABLE OILS, INC., Torrance, CA (US)

( * ) Notice: Subject to any disclaimer, the term of this patent is extended or adjusted under 35 U.S.C. 154(b) by 34 days.

(21) Appl. No.: 17/168,561

(22) Filed: Feb. 5, 2021

(65) Prior Publication Data

US 2022/0167578 A1 Jun. 2, 2022

Related U.S. Application Data (60) Provisional application No. 63/120,276, filed on Dec. 2, 2020.

(51) Int. Cl.
*A01H 5/10* (2018.01)
*A01H 6/20* (2018.01)

(52) U.S. Cl.
CPC .................. *A01H 6/20* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 8,319,020 B2 | 11/2012 | Guillen-Portal | |
| 8,319,021 B2 * | 11/2012 | Guillen-Portal | A01H 6/20 435/430 |
| 8,324,458 B2 | 12/2012 | Guillen-Portal | |
| 2009/0151028 A1 | 6/2009 | Kuvshinov et al. | |

OTHER PUBLICATIONS

Righini et al, Industrial Crops and Prods 137: 66-73, 2019 (Year: 2019).*
Kuan, L., et al. "Metabolic Engineering a Model Oilseed Camelina sativa for the Sustainable Production of High-Value Designed Oils." Frontiers in Plant Science, 2020, 11(11): 1-14.

* cited by examiner

*Primary Examiner* — Elizabeth F McElwain
(74) *Attorney, Agent, or Firm* — Saliwanchik, Lloyd & Eisenschenk (57) ABSTRACT

The subject invention relates to a *Camelina sativa* (L.) Crantz spring-type seed designated as "SO-100" derived from a cross between *camelina* accessions with high yield and oil quality attributes following conventional breeding methodologies.

20 Claims, 2 Drawing Sheets

FIG. 1

| Variety | Linear regression coefficient Slope (b) | Residual variance Sigma$^2$ (x1000) | Average grain yield | Low-yielding envt. | High-yielding envt. |
|---|---|---|---|---|---|
| | | | ---------- Lb/ac ---------- | | |
| SO-100 | 1.03 | 29.41 | 1556 | 761 | 2232 |
| Calena | 0.96 | 10.89 | 1417 | 747 | 2240 |
| Blaine Creek | 1.01 | 24.03 | 1357 | 683 | 2516 |
| Mean | | | 1443 | 730 | 2329 |

FIG. 2

CAMELINA SATIVA VARIETY "SO-100"

CROSS-REFERENCE TO RELATED APPLICATION

This application claims priority to U.S. Provisional Patent App. No. 63/120,276, filed Dec. 2, 2020, which is incorporated herein by reference in its entirety.

BACKGROUND

Current trends in the international petroleum market and concerns on the excessive use of petroleum-derived fuels on the environment have led to increased interest in the development and adoption of renewable sources of energy in the USA. In some instances this has derived in the adoption of government policies, like the Energy Independency and Security Act of 2007 (Public Law 110-140, 2007), in others in the take-over of private initiatives like that aimed at using plant-derived renewable fuels to partly satisfy the fuel demand of the aviation industry (Anonymous, 2009).

Among the several types of feedstocks proposed for the production of renewable fuel, use of industrial-grade oilseed crops are considered a viable option. Camelina (*Camelina sativa*, (L.) Crantz), an annual plant that belongs to the Brassicaceae family, is an oilseed crop that can produce decent yields under relative low inputs, exhibits a broad adaptability to a range of environmental conditions, and its seeds contain a relatively high amount of oil (Putnam et al., 1993; Budin et al., 1995; Vollman et al., 1996; Gugel and Falk, 2006). In addition, studies on the impact of *camelina*-derived fuel on the environment indicates that use of this fuel can reduce carbon emissions by up to 80% (Shonnard et al., 2010) conferring this crop a potential to be used as biofuel feedstock crop.

Although *camelina* is a plant with a rich history (Schultze-Motel, J., 1979; Bouby, 1998), in general little genetic improvement has been practiced on this crop. In the USA, although efforts were devoted to this crop in the past (Porcher, 1863, Robinson, 1987), currently the number of varieties available for commercial production is very limited. Consequently, there is a real need to develop *camelina* varieties with high productivity and broad adaptability, especially to low-input agricultural systems in the USA, to be used as reliable, commercial feedstocks for the emerging biofuel industry.

The main object of the invention is to provide seed of a superior *camelina* variety that provides high and stable yields and is suitable of commercial production under high- and/or low-input conditions in agricultural areas in various temperate regions.

Another object is to provide seed of a *camelina* variety that exhibits acceptable and stable agronomic characteristics.

BRIEF SUMMARY OF THE INVENTION

The subject invention provides *camelina* plants having unique reproductive attributes associated with grain and oil yield superiority, and the ability to grow efficiently and consistently under dryland, high-input and/or low-input conditions. The subject invention also provides methods of producing the *camelina* plants, as well as methods of introducing one or more desired traits into the *camelina* plants.

In preferred embodiments, the *camelina* plants of the subject invention are of the *Camelina sativa* (L.) variety. In specific preferred embodiments, the *Camelina sativa* (L.) variety is the *camelina* plant designated as "SO-100," a representative seed sample of which has been deposited under ATCC Accession No. PTA-126938 on Dec. 18, 2020.

In some embodiments, the *camelina* plant is a plant having one or more, or all the physiological and morphological characteristics of *Camelina sativa* (L.) variety "SO-100." In some embodiments, the *camelina* plant is derived from a cross between a first parent *camelina* plant and a second parent *camelina* plant, wherein the first and/or second parent *camelina* plants are *Camelina sativa* (L.) variety "SO-100," or *camelina* plants having one or more, or all, of the physiological and morphological characteristics of *Camelina sativa* (L.) variety "SO-100."

In preferred embodiments, the *camelina* plants of the subject invention have high grain and oil yields compared to a check line of *camelina*. In some embodiments, the check line is, for example, Calena, Ligena, Blaine Creek, Cs11, Cs21, Celine, Galena, Robinson, and/or Suneson.

In certain embodiments, the *camelina* plants of the subject invention have higher grain and oil yields when compared with the proprietary *Camelina sativa* (L.) variety "SO-50," a description of which can be found in U.S. Pat. No. 8,319,021 (incorporated by reference herein).

In some embodiments, the *camelina* plants of the subject invention are developed through conventional breeding methods, having the ability to grow efficiently and consistently under dryland, high-input and/or low-input conditions.

In some embodiments, the distinctive features of the subject plants compared to a check line include one or more of: a relatively lower seed oil content (e.g., about 35%), a relatively taller plant height (e.g., about 33 inches), a higher grain yield (e.g., about 1,556 lb/ac) and a higher oil yield (e.g., about 554 lb/ac) compared with other check varieties. Additionally, the plants are stable in their performance across a wide range of environmental conditions (see FIGS. 1-2).

In certain embodiments, the subject invention also provides plant parts of the subject *camelina* plants. Plant parts can include, for example, the shoot, root, stem, seeds, racemes, stipules, leaves, petals, flowers, ovules, bracts, branches, petioles, internodes, pollen, stamen, or the like.

In some embodiments, the plant part is the seed of the *camelina* plant designated as "SO-100" (ATCC No. PTA-126938).

In certain embodiments, the subject invention also provides plant cells of the subject *camelina* plants. In some embodiments, the plant cell(s) can be cultured and used to produce a *camelina* plant having one or more, or all, of the physiological and morphological characteristics of the subject *camelina* plants.

In certain embodiments, the subject invention also provides tissue culture of the subject *camelina* plants. In some embodiments, the tissue culture(s) are produced from a plant part such as, for example, embryos, meristematic cells, leaves, pollen, root, root tips, stems, anther, pistils, pods, flowers, and seeds. In some embodiments, the tissue culture can be used to regenerate a *Camelina sativa* (L.) plant, said plant having the morphological and physiological characteristics of *Camelina sativa* (L.) variety "SO-100" (ATCC No. PTA-126938).

In certain embodiments, the subject invention provides methods of producing the subject *camelina* plants. In some embodiments, the plants are produced through conventional breeding methods.

In certain embodiments, the subject invention provides methods for producing a *camelina* seed. In some embodiments, the methods comprise crossing a first parent *camelina* plant with a second parent *camelina* plant and harvesting the resultant hybrid seed, wherein the first parent *camelina* plant and/or second parent *camelina* plant is a *Camelina sativa* (L.) plant of the subject invention.

In certain embodiments, the subject invention provides methods for introducing one or more desired traits into the subject *camelina* plants.

In some embodiments, the methods comprise introducing one or more transgenes into the genome of the subject *camelina* plants. In some embodiments, the methods comprise crossing the *camelina* plants of the subject invention to one or more transgenic plants, wherein the transgenic plants comprise one or more transgenes.

In some embodiments, the transgene is a gene for herbicide resistance in a plant, and the herbicide is selected from the group consisting of imidazolinone, sulfonylurea, glyphosate, glufosinate, L-phosphinothricin, triazine, sethoxydim, and benzonitrile. In some embodiments, the transgene is a gene for insect resistance in a plant, for example, the transgene encodes a *Bacillus thuringiensis* endotoxin. In some embodiments, the transgene is a gene for disease resistant in a plant. In some embodiments, the transgene is a gene for water stress tolerance, heat tolerance, improved shelf life, and/or improved nutritional quality.

In some embodiments, the methods for introducing one or more desired traits into the subject *camelina* plants comprise:

(a) crossing a *camelina* plant of the subject invention with another *camelina* plant that comprises a desired trait to produce F1 progeny plants;

(b) selecting one or more progeny plants that have the desired trait to produce selected progeny plants;

(c) crossing the selected progeny plants with the *camelina* plant of the subject invention to produce backcross progeny plants;

(d) selecting for backcross progeny plants that have the desired trait and physiological and morphological characteristics of the *camelina* plant of the subject invention to produce selected backcross progeny plants; and (e) optionally, repeating steps (c) and (d) three or more times in succession to produce selected fourth or higher backcross progeny plants that comprise the desired trait and the physiological and morphological characteristics of the *camelina* plant of the subject invention.

In some embodiments, the desired trait is, for example, selected from the group consisting of insect resistance, disease resistance, water stress tolerance, heat tolerance, improved shelf life, and improved nutritional quality.

DETAILED DESCRIPTION OF THE INVENTION

The subject invention provides *camelina* plants having reproductive attributes that lead to high grain yield and high oil yield, and the ability to grow efficiently and consistently under dryland, high-input and/or low-input conditions. The subject invention also provides methods of producing the *camelina* plants, as well as methods of introducing one or more desired traits into the *camelina* plants.

Selected Definitions

As used herein:

"Days to 50% flowering" refers to period from germination of the seed to the manifestation of flowering in 50% of the plant population;

"Days to Maturity" refers to the period from germination of the seed to the period when fully developed seeds where developed in 50% of the plant population;

"Seed filling days" refers to the period from the beginning of seed growth until the seed is fully developed and has reached maximum dry weight;

"Plant height" refers to the height of the adult plant from the ground base where it is being grown to the tip of the main raceme;

"Racemes per plant" refers to the number of reproductive branches derived from the main stem of the plant;

"Main raceme length" refers to the length of the terminal raceme in the plant;

"Inflorescence length" refers to the length of the main inflorescence from its base to the tip of the terminal raceme;

"Inflorescence diameter" refers to the diameter of the inflorescence at its widest plane and is measured right after flowering has been completed;

"Pod number" refers to the total number of pods in the plant bearing seeds;

"Pod weight" refers to the weight of a pod once the plant has reached maturity and consequently is ready to be harvested;

"Seeds per pod" refers to the number of fully developed seed contained inside a pod in the plant;

"Seeds per plant" refers to the total number of fully developed seeds the plant has produced;

"Seed weight" refers to the total weight of a fully developed seed, usually expressed in weight per thousand seeds;

"Test weight" refers to a measure of the seed weight in pounds for a given bushel volume;

"Grain yield" refers to a measure of the harvested clean seed weight in pounds in one acre of land area;

"Oil content" refers to the fraction of total oil contained in the mature seed; "Oil yield" refers to a measure of the seed oil weight collected in pounds in one acre of land area;

"Variety" refers to a homogeneous, highly homozygous group of individuals that are genetically distinct from other groups of individuals within the species;

"Cross" refers to the process by which pollen from one flower from a plant is artificially transferred to the stigma from the flower of another plant;

"Progeny" refers to the offspring derived from an artificial cross between two plants;

"Selfing" refers to the manifestation of the process of self-pollination, which in turn refers to the transfer of pollen from the anther of a flower to the stigma of the same flower or different flowers on the same plant;

"Single plant selection" refers to a form of selection in which plants with specific desirable attributes are identified and individually selected; and "Seed increase" refers to the process of sowing, growing and harvesting seed from a specific plant material for the purpose of creating a larger volume of seed.

As used herein, the term "plant" refers to any living organism belonging to the kingdom Plantae (i.e., any genus/species in the Plant Kingdom). In preferred embodiments, the plant is a species in the tribe of Camelineae, such as

*Camelina alyssum*, *C. anomala*, *C. grandiflora*, *C. hispida*, *C. laxa*, *C. microcarpa*, *C. microphylla*, *C. persistens*, *C. rumelica*, *C. sativa*, *C. Stiefelhagenii*, and/or any hybrid thereof.

As used herein, the terms "plant part" and "plant tissue" are used interchangeably and refer to any portion(s) of a plant including, but not limited to, the shoot, root, stem, seeds, racemes, stipules, stalks, leaves, petals flowers, ovules, bracts, branches, petioles, internodes, tiller, pollen, stamen, and the like. "Aerial" plant parts refer to above-ground plant parts, which can also be referred to as "shoots." "Subterranean" plant parts refer to below-ground plant parts, which can also be referred to as "roots."

As used herein, the term "cross," "crossing," "cross-pollination" or "cross-breeding" refer to the process by which the pollen of one flower on one plant is applied (artificially or naturally) to the ovule (stigma) of a flower on another plant.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

*Camelina* Sativa

*Camelina sativa*, known in English as *camelina*, gold-of-pleasure, false flax, wild flax, linseed dodder, German sesame, and Siberian oilseed, is a flowering plant in the family Brassicaceae, which includes, for example, mustard, cabbage, rapeseed, broccoli, cauliflower, kale, and brussels sprouts. *Camelina* is native to Northern Europe and to Central Asia, but has been introduced to North America, possibly as a weed in flax imports.

The crop is now being researched due to its exceptionally high levels (up to 45%) of omega-3 fatty acids, which is uncommon in vegetable sources. The fatty acid composition of *camelina* comprises high levels of polyunsaturated fatty acids, such as C18:2 and C18:3 fatty acids (52-54%), as well as long chain fatty acids, such as C20:1 (11-15%) and C22:1 (2-5%) fatty acids.

*Camelina* oil is well-suited for use as a cooking oil. It has an almond-like flavor and aroma. The major components of *camelina* oil are alpha-linolenic acid (C18:3 (omega-3-fatty acid, approximately 35-45%) and linoleic acid (C18:2 (omega-6 fatty acid, approximately 15-20%)). *Camelina* oil is also very rich in natural antioxidants, such as tocopherols, which contributes to the highly stable character of the oil, as well as its resistance to oxidation and rancidity. Other components of *camelina* oil include, for example, erucic acid (1-3%) and vitamin E (about 110 mg/100 g). (Pilgeram et al., 2007; Vollmann et al. 1996; Putnam et al., 1993; Berti and Schneiter, 1993; Pavlista and Baltensperger, 2007).

In addition to its oil, *camelina* plant parts can be used as commercial feed, as well as to produce useful chemicals, for example, camalexins (Browne et al., 1991).

Methods of transforming *camelina* plants have been described in US20040031076, US20090151028, US20090151023, WO/2002/038779A1, and WO/2009/117555A1, each of which is incorporated by reference in its entirety.

Methods for *camelina* tissue culture have been described previously. For example, *Camelina sativa* shoots have been regenerated from leaf explants (Tattersall and Millam, Plant Cell Tissue and Organ Culture 55:147-149, 1999). *Camelina sativa* has also been used in a somatic fusion with other *Brassica* species (Narasimhulu et al., Plant Cell Rep. 13:657-660, 1994; Hansen, Crucifer. News 19:55-56, 1997; Sigareva and Earle, Theor. Appl. Genet. 98:164-170, 1999) and regenerated interspecific hybrid plants were obtained (Sigareva and Earle).

More tissue culture techniques for *Camelina* can be found in Bhojwani and Razdan (Plant tissue culture: theory and practice, Elsevier, 1996, ISBN 97804448162328), Trigiano and Gray (Plant tissue culture concepts and laboratory exercises, Volume 1999, CRC Press, 2000, ISBN 0849320291, 9780849320293), Kumar (Plant Tissue Culture And Molecular Markers: Their Role In Improving Crop Productivity, I. K. International Pvt Ltd, 2009, ISBN 8189866109, 9788189866105), George et al., (Plant Propagation by Tissue Culture 3rd Edition: Volume 1. the Background, ISBN 1402050046, 9781402050046). Sathyanarayana (Plant Tissue Culture: Practices and New Experimental Protocols, I. K. International Pvt Ltd, 2007, ISBN 8189866117, 9788189866112), Pierik (In vitro culture of higher plants, Springer, 1997, ISBN 0792345274, 9780792345275), and Vasil (Plant cell and tissue culture, Springer, 1994, ISBN 0792324935, 9780792324935), each of which is incorporated by reference in its entirety herein for all purposes.

*Camelina sativa* (L.) Variety "SO-100"

*Camelina sativa* (L.) variety "SO-100" is a true-bred *camelina* selected from a cross between accession "A3U7761," a material originated in Austria, and accession "Ames 26676," a material originated in the former Soviet Union. A representative sample of seeds of "SO-100" has been deposited under ATCC Accession No. PTA-126938 on Dec. 18, 2020.

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are several primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. Third, a method used in plant species that are largely self-pollinated in nature, such as soybeans, wheat, rice, safflower, *camelina* and others is pedigree selection. In this situation, crosses are made and individual plants and lines from individual plants are selected for desired traits. These lines are then advanced as genetically homogeneous varieties. Since the individuals are largely self-pollinated these lines are analogous to an inbred line with favorable agronomic characteristics. These plant breeding procedures for improving open-pollinated populations are well known to those skilled in the art and comprehensive reviews of breeding procedures routinely used for improving cross-pollinated plants are provided in numerous texts and articles, including: Allard, Principles of Plant Breeding, John Wiley & Sons, Inc. (1960); Simmonds, Principles of Crop Improvement, Longman Group Limited (1979); Hallauer and Miranda, Quantitative Genetics in Maize Breeding, Iowa State University Press (1981); and, Jensen, Plant Breeding Methodology, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed varieties. A pedigreed variety is a superior genotype developed from selection of individual plants out of a segregating population followed by propagation and seed increase of self-pollinated offspring and careful testing of the genotype over several generations. This is an open pollinated method that works well with naturally self-pollinating species. This method can be used in combination with mass selection in variety development. Variations in pedigree and mass selection in combination are the most common methods for generating varieties in self-pollinated crops.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, In Hybridization of Crop Plants.

Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, READ BOOKS, 2007, ISBN 1406737062, 9781406737066), and Lorz et al. (Molecular marker systems in plant breeding and crop improvement, Springer, 2005, ISBN 3540206892, 9783540206897), each of which is incorporated by reference in its entirety.

DEPOSIT INFORMATION

A deposit of the seed of Camelina saliva (L.) variety "SO-100" is maintained by Sustainable Oils, Inc., 2790 Skypark Dr. Suite 105, Torrance, Calif. 90505, USA. In addition, a sample of the seed of Camelina sativa (L.) variety "SO-100" has been deposited by Sustainable Oils, Inc., with American Type Culture Collection (ATCC), 10801 University Blvd. Manassas, Va. 20110-2209, USA.

To satisfy the enablement requirements of 35 U.S.C. § 112, and to certify that the deposit of the seeds of the present invention meets the criteria set forth in 37 C.F.R. §§ 1.801-1.809, Applicants hereby make the following statements regarding the deposited seed of Camelina sativa (L.) variety "SO-100" (deposited as ATCC Accession No. PTA-126938 on Dec. 18, 2020):

1. During the pendency of this application, access to the invention will be afforded to the Commissioner upon request;
2. Upon granting of the patent the strain will be available to the public under conditions specified in 37 CFR § 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same seed source with ATCC. The Applicant does not waive any infringement of their rights granted under this patent or under the Plant Variety Protection Act (7 U.S.C. § 2321 et seq.). U.S. Plant Variety Protection of SO-100 is being applied for. Unauthorized seed multiplication prohibited.

EXAMPLES

It should be understood that the examples and embodiments described herein are for illustrative purposes only and that various modifications or changes in light thereof will be suggested to persons skilled in the art and are to be included within the spirit and purview of this application.

Example 1—Testing of Seed Quality Traits

The present invention is based on the development of true-bred camelina seeds with unique characteristics, including, for example, decreased seed oil content and taller plant height. Advantageously, in some embodiments, the unique characteristics include, and/or contribute to, increased oil and grain yields.

The oil content in the camelina seed was determined using contiguous wave low-resolution nuclear magnetic resonance (NMR) spectrometry at the Seed Lab at Oregon State University (Seed Science & Technology, Department of Crop and Soil Sciences, Oregon State University, Corvallis, Oreg., 97331).

Example 2—Agronomic Performance Field Evaluation of Camelina sativa (L.) SO-100

During the spring of 2010, 2011, and 2019, the performance of SO-100 was evaluated in representative areas within the Pacific Northwest and the Northern High Plains of the U.S., including Oregon (Pendleton), Montana (Amsterdam, Bozeman, Huntley, Moccasin and Havre), Nebraska (Scottsbluff), Washington (Dusty), Wyoming (Lingle) and North Dakota (Carrington).

Two standard camelina varieties, "Calena" and "Blaine Creek" were included in these trials as controls for comparative purposes. These evaluations were carried out under standard production practices.

Combined across all years and all environments, the average grain yield for SO-100 was 1,556 Lb/ac (range of 761 to 2,599 Lb/ac), which was 9.8% higher than the mean yield of Calena (1,417 Lb/ac; range of 747 to 2,240 Lb/ac) and 14.7% higher than Blaine Creek (1,357 Lb/ac; range of 683 to 2,516 Lb/ac) (Table 1).

Figure 1:
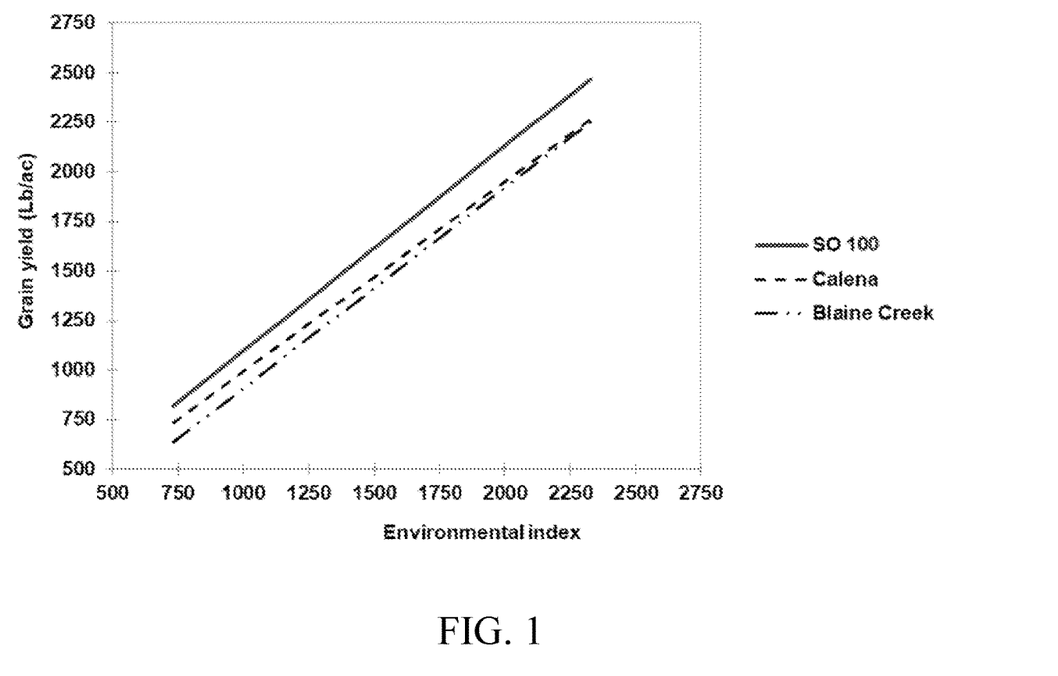
FIG. 1 shows a stability of performance curve for SO-100, Calena and Blaine Creek varieties.
Figure 2:
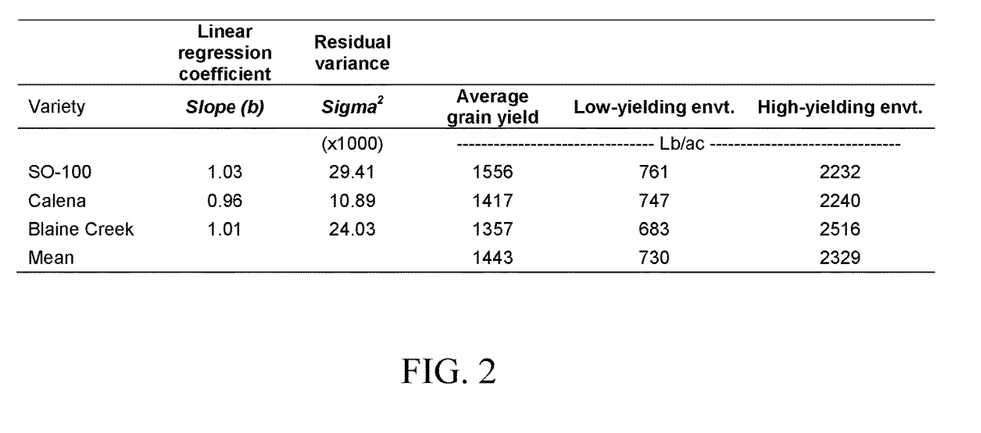
FIG. 2 shows the linear regression coefficient and residual variance from stability of performance analyses of SO-100, Blaine Creek and Calena according to Finlay and Wilkinson (1963) and Eberhart and Russell (1966).

SO-100 has a linear stability coefficient (b) of 1.03 and a variance deviation from linear regression ($\sigma^2$) of 29410 according to Finlay and Wilkinson (1963) and Eberhart and Russell (1966) (FIGS. 1-2). Thus, variety SO-100 should be considered a high-yielding variety with broad adaptability to high- and low-input growing conditions.

Combined across all years and all environments, the average seed oil content of SO-100 was 34.9% (range of 24.8 to 41.1%), which was 2.0% lower than the average seed oil content of Calena (35.6%, range of 27.4 to 42%) and 3.3% lower than Blaine creek (36.1%, range of 28.5 to 42.4%) (Table 2). However, the average oil yield for SO-100 was 554 Lb/ac (range of 187 to 1,027 Lb/ac), which was 8.2% higher than the mean yield of Calena (512 Lb/ac; range of 205 to 888 Lb/ac) and 11.0% higher than Blaine Creek (499 Lb/ac; range of 195 to 906 Lb/ac) (Table 3). Thus, SO-100 should be considered a higher oil-yielding variety.

In general, other than a relatively taller plant height (about 34 inches), SO-100 exhibited agronomic and phenologic characteristics that were comparable to the control varieties (Tables 4-8).

TABLE 1

Grain yield (Lb/ac) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | 1302 | 2599 | 1102 | 2342 | 1808 | 1356 | 1702 | 1595 | 1250 |
| Calena | 954 | 2065 | 981 | 2228 | 1558 | 1484 | 1395 | 1374 | 1100 |
| Blaine Creek | 852 | 1968 | 1025 | 1678 | 1645 | 1401 | 1868 | 1202 | 872 |
| Mean | 1036 | 2210 | 1036 | 2083 | 1670 | 1414 | 1655 | 1391 | 1074 |
| p value | ** | NS | NS | NS | NS | NS | NS | * | * |
| CV (%) | 9 | 11 | 18 | 17 | 12 | 8 | 13 | 10 | 11 |
| LSD (0.05) | 221.8 | — | — | — | — | — | — | 241.8 | 212.3 |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 1439 | 1779 | 1588 | 914 | 1122 | 2232 | 761 | 1556 |
| Calena | 1440 | 1373 | 1701 | 776 | 1256 | 2240 | 747 | 1417 |
| Blaine Creek | 1112 | 1218 | 1717 | 714 | 1236 | 2516 | 683 | 1357 |
| Mean | 1330 | 1457 | 1669 | 801 | 1205 | 2329 | 730 | 1443 |
| p value | NS | NS | NS | NS | NS | NS | NS | *** |
| CV (%) | 13 | 27 | 11 | 17 | 14 | 7 | 14 | 14 |
| LSD (0.05) | — | — | — | — | — | — | — | 79.6 |

\*, \*\*, \*\*\* Significant at the 0.05, 0.01, and 0.001 probability levels.
NS Not significant.

TABLE 2

Seed oil content (%) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | 39.2 | 39.5 | 33.6 | 39.0 | 39.3 | 33.2 | 37.1 | 34.2 | 27.9 |
| Calena | 40.0 | 39.8 | 34.8 | 40.2 | 39.2 | 32.9 | 36.7 | 34.8 | 29.1 |
| Blaine Creek | 40.4 | 39.7 | 35.7 | 40.8 | 40.3 | 31.2 | 37.5 | 35.7 | 29.9 |
| Mean | 39.9 | 39.7 | 34.7 | 40.0 | 39.6 | 32.4 | 37.1 | 34.9 | 29.0 |
| p value | NS | NS | NS | NS | NS | NS | NS | * | NS |
| CV (%) | 1 | 1 | 3 | 2 | 3 | 4 | 1 | 2 | 3 |
| LSD (0.05) | — | — | — | — | — | — | — | 0.9 | — |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 36.6 | 31.9 | 41.1 | 32.8 | 34.0 | 34.1 | 24.8 | 34.9 |
| Calena | 35.5 | 33.0 | 42.0 | 35.1 | 35.2 | 33.8 | 27.4 | 35.6 |
| Blaine Creek | 37.3 | 33.2 | 42.4 | 35.2 | 33.9 | 35.5 | 28.5 | 36.1 |
| Mean | 36.5 | 32.7 | 41.8 | 34.4 | 34.4 | 34.5 | 26.9 | 35.5 |
| p value | ** | NS | NS | NS | NS | NS | NS | NS |
| CV (%) | 1 | 2 | 2 | 3 | 7 | * | 8 | 3 |
| LSD (0.05) | 0.9 | — | — | — | — | 1.0 | — | — |

\*, \*\* Significant at the 0.05 and 0.01 probability levels.
NS Not significant.

TABLE 3

Oil yield (Lb/ac) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | 512 | 1027 | 371 | 914 | 708 | 449 | 632 | 546 | 349 |
| Calena | 382 | 822 | 339 | 888 | 614 | 489 | 510 | 479 | 320 |
| Blaine Creek | 345 | 781 | 365 | 683 | 664 | 440 | 697 | 430 | 261 |
| Mean | 413 | 877 | 358 | 828 | 662 | 459 | 613 | 485 | 310 |
| p value | ** | NS | NS | NS | NS | * | NS | * | NS |
| CV (%) | 10 | 11 | 17 | 14 | 13 | 12 | 13 | 11 | 13 |
| LSD (0.05) | 97.7 | — | — | — | — | — | — | 90.5 | — |

TABLE 3-continued

Oil yield (Lb/ac) of camelina variety SO-100 and other control camelina varieties.

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 526 | 567 | 653 | 300 | 381 | 744 | 178 | 554 |
| Calena | 492 | 453 | 715 | 274 | 443 | 764 | 205 | 512 |
| Blaine Creek | 415 | 404 | 727 | 252 | 425 | 906 | 195 | 499 |
| Mean | 477 | 475 | 698 | 276 | 417 | 805 | 195 | 522 |
| p value | NS | NS | NS | NS | NS | * | NS | *** |
| CV (%) | 14 | 27 | 10 | 19 | 19 | 8 | 11 | 14 |
| LSD (0.05) | — | — | — | — | — | 138.6 | — | 29.5 |

*, , * Significant at the 0.05, 0.01, and 0.001 probability levels.
NS Not significant.

TABLE 4

Days to 50% flowering of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | — | 51 | 72 | 70 | 68 | 67 | — | 51 | 44 |
| Calena | — | 50 | 73 | 72 | 69 | 67 | — | 51 | 43 |
| Blaine Creek | — | 50 | 72 | 70 | 68 | 66 | — | 49 | 43 |
| Mean | — | 50 | 72 | 71 | 68 | 67 | — | 50 | 43 |
| p value | — | NS | NS | NS | NS | NS | — | ** | * |
| CV (%) | — | 1 | 1 | 3 | 1 | 1 | — | 1 | 1 |
| LSD (0.05) | — | — | — | — | — | — | — | 0.6 | 0.7 |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 63 | 85 | — | 56 | 63 | 56 | — | 62 |
| Calena | 62 | 85 | — | 56 | 64 | 58 | — | 63 |
| Blaine Creek | 62 | 84 | — | 55 | 61 | 56 | — | 62 |
| Mean | 62 | 85 | — | 56 | 63 | 56 | — | 62 |
| p value | NS | NS | — | NS | * | ** | — | ** |
| CV (%) | 1 | 1 | — | 1 | 1 | 1 | — | 1 |
| LSD (0.05) | — | — | — | — | 1.5 | 1.0 | — | 0.3 |

*, ** Significant at the 0.05 and 0.01 probability levels.
NS Not significant.

TABLE 5

Seed filling days of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | — | 27 | 35 | 38 | 36 | — | — | 33 | 28 |
| Calena | — | 28 | 33 | 39 | 36 | — | — | 33 | 29 |
| Blaine Creek | — | 28 | 35 | 36 | 36 | — | — | 34 | 28 |
| Mean | — | 28 | 34 | 38 | 36 | — | — | 33 | 28 |
| p value | — | NS | NS | NS | NS | — | — | * | NS |
| CV (%) | — | 8 | 5 | 3 | 2 | — | — | 2 | 3 |
| LSD (0.05) | — | — | — | — | — | — | — | 1.0 | — |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 33 | 28 | — | 30 | 26 | 33 | — | 32 |
| Calena | 33 | 28 | — | 34 | 25 | 33 | — | 32 |
| Blaine Creek | 33 | 27 | — | 32 | 27 | 33 | — | 32 |
| Mean | 33 | 28 | — | 32 | 26 | 33 | — | 32 |
| p value | NS | NS | — | NS | NS | NS | — | NS |
| CV (%) | 5 | 3 | — | 7 | 3 | 4 | — | 4 |
| LSD (0.05) | — | — | — | — | — | — | — | — |

* Significant at the 0.05 probability levels.
NS Not significant.

TABLE 6

Plant height (inches) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | — | 33 | 32 | 38 | 39 | 28 | — | 27 | 34 |
| Calena | — | 29 | 31 | 35 | 40 | 28 | — | 26 | 33 |
| Blaine Creek | — | 31 | 31 | 33 | 39 | 27 | — | 25 | 30 |
| Mean | — | 31 | 31 | 35 | 39 | 28 | — | 26 | 32 |
| p value | — | NS | NS | NS | NS | NS | — | * | NS |
| CV (%) | — | 7 | 3 | 6 | 5 | 7 | — | 3 | 9 |
| LSD (0.05) | — | — | — | — | — | — | — | 1.5 | — |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 27 | 32 | 35 | 28 | 36 | 37 | 30 | 33 |
| Calena | 29 | 29 | 34 | 29 | 38 | 33 | 28 | 32 |
| Blaine Creek | 27 | 29 | 36 | 29 | 35 | 36 | 29 | 31 |
| Mean | 28 | 30 | 35 | 29 | 36 | 35 | 29 | 32 |
| p value | NS | NS | NS | NS | NS | NS | NS | NS |
| CV (%) | 10 | 7 | 5 | 7 | 5 | 7 | 3 | 7 |
| LSD (0.05) | — | — | — | — | — | — | — | — |

* Significant at the 0.05 probability levels.
NS Not significant.

TABLE 7

Seed weight (g/1000) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | 1.39 | 1.46 | 1.29 | 1.47 | 1.43 | 1.51 | 1.35 | 1.19 | 0.93 |
| Calena | 1.36 | 1.41 | 1.34 | 1.48 | 1.33 | 1.55 | 1.41 | 1.17 | 0.95 |
| Blaine Creek | 1.36 | 1.43 | 1.33 | 1.55 | 1.21 | 1.47 | 1.37 | 1.12 | 0.90 |
| Mean | 1.37 | 1.43 | 1.32 | 1.50 | 1.32 | 1.51 | 1.38 | 1.16 | 0.93 |
| p value | NS | NS | NS | NS | * | NS | NS | NS | NS |
| CV (%) | 6 | 4 | 5 | 11 | 5 | 5 | 7 | 4 | 7 |
| LSD (0.05) | — | — | — | — | 0.1 | — | — | — | — |

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 1.14 | 1.04 | 1.19 | — | — | — | — | 1.28 |
| Calena | 1.11 | 1.04 | 1.18 | — | — | — | — | 1.28 |
| Blaine Creek | 1.05 | 0.95 | 1.15 | — | — | — | — | 1.24 |
| Mean | 1.10 | 1.01 | 1.17 | — | — | — | — | 1.27 |
| p value | NS | * | NS | — | — | — | — | NS |
| CV (%) | 9 | 3 | 3 | — | — | — | — | 7 |
| LSD (0.05) | — | 0.1 | — | — | — | — | — | — |

* Significant at the 0.05 probability levels.
NS Not significant.

TABLE 8

Test weight (Lb/Bu) of camelina variety SO-100 and other control camelina varieties.

| Variety | Bozeman 2010 | Carrington 2010 | Dusty 2010 | Havre 2010 | Huntley 2010 | Lingle 2010 | Pendleton 2010 | Amsterdam 2011 | Carrington 2011 |
|---|---|---|---|---|---|---|---|---|---|
| SO-100 | 52.6 | 53.1 | — | 52.6 | 52.5 | — | — | 51.8 | 49.7 |
| Calena | 52.9 | 52.9 | — | 52.4 | 52.5 | — | — | 51.8 | 49.5 |
| Blaine Creek | 52.9 | 52.7 | — | 52.4 | 52.4 | — | — | 51.7 | 48.4 |
| Mean | 52.8 | 52.9 | — | 52.5 | 52.5 | — | — | 51.8 | 49.2 |
| p value | NS | NS | — | NS | NS | — | — | NS | ** |
| CV (%) | 1 | 1 | — | <1 | <1 | — | — | 1 | 1 |
| LSD (0.05) | — | — | — | — | — | — | — | — | 0.9 |

TABLE 8-continued

Test weight (Lb/Bu) of camelina variety SO-100 and other control camelina varieties.

| Variety | Havre 2011 | Huntley 2011 | Pendleton 2011 | Huntley 2019 | Moccasin 2019 | Pendleton 2019 | Scottsbluff 2019 | Combined |
|---|---|---|---|---|---|---|---|---|
| SO-100 | 52.3 | 51.4 | 52.2 | 44.1 | 47.9 | 51.6 | — | 51.0 |
| Calena | 52.0 | 50.5 | 52.3 | 46.7 | 50.9 | 52.1 | — | 51.4 |
| Blaine Creek | 51.9 | 51.1 | 52.1 | 45.2 | 50.4 | 52.2 | — | 51.1 |
| Mean | 52.1 | 51.0 | 52.2 | 45.3 | 49.7 | 51.9 | — | 51.2 |
| p value | NS | NS | NS | NS | NS | NS | — | ** |
| CV (%) | 1 | 2 | <1 | 3 | 1 | 1 | — | 1 |
| LSD (0.05) | — | — | — | — | — | — | — | 0.2 |

*, ** Significant at the 0.05, 0.01 probability levels.
NS Not significant.

Example 4—Development of SO-100

The present invention involves the development of true-bred *camelina* seeds capable of growing and providing adequate seed yields under high-input, low-input, and/or dryland conditions in North America and other temperate regions, and having, but not being limited to, one or more of the following characteristics compared to other popular *camelina* varieties:

(i) a lower seed oil content of about, e.g., 34.9% (range of 27.9 to 41.1%);
(ii) a medium flowering period of about, e.g., 62 DAP (range of 44 to 85 DAP);
(iii) a medium seed filling period of about, e.g., 32 days (range of 26 to 38 days);
(iv) a medium to high seed weight of about, e.g., 1.28 g/1,000 seeds (range of 0.93 to 1.51 g/1,000);
(v) a medium to high plant height of about, e.g., 33 inches/83.8 cm (range of 27 to 39 inches (68.6 to 99.1 cm);
(vi) a high oil yield of about, e.g., 554 Lb/ac (range of 187 to 1,027 Lb/ac); and
(vii) a high grain yield of about, e.g., 1,556 Lb/ac (range of 761 to 2,599 Lb/ac).

Variety "SO-100" was developed from a cross between accession "A3U7761," a material originated in Austria, and accession "Ames 26676," a material originated in the former Soviet Union. These accessions were evaluated for agronomic performance, adaptability, and oil quality attributes (fatty acid profile) across multiple locations during the period of 2006-2009 (Tables 9 and 10).

TABLE 9

Specifics on field evaluations of parental accessions "A3U7761" and "Ames26676"

| Set | Entries | Year | Season | Site(s)[†] |
|---|---|---|---|---|
| 1 | 33 | 2006 | Spring | 8 |
| 2 | 45 | 2007 | Spring | 5 |
| 3 | 12 | 2007 | Spring | 11 |
| 4 | 20 | 2007/2008 | Winter | 1 |
| 5 | 20 | 2008 | Spring | 25 |
| 6 | 20 | 2008 | Spring | 5 |
| 7 | 20 | 2008/2009 | Winter | 1 |
| 8 | 21 | 2009 | Spring | 7 |
| 9 | 20 | 2009 | Spring | 16 |

[†]Sites covered representative areas AZ, ID, MT, ND, NE, NM, OR, SD, WA, and WY in the USA, and in Alberta, Manitoba, and Saskatchewan, in Canada

TABLE 10

Agronomic performance of parental accessions A3U7761 and Ames 26676.

| Accession | Set 1 | Set 2 | Set 3 | Set 4 | Set 5 | Set 6 | Set 7 | Set 8 | Set 9 | Mean |
|---|---|---|---|---|---|---|---|---|---|---|
| Grain yield (Lbs/ac) | | | | | | | | | | |
| A3U7761 | 1408 | 1731 | 1446 | 1728 | 1394 | 1868 | 1209 | 1725 | 1720 | 1581 |
| Ames 26676 | 1283 | 1657 | 1290 | 1253 | 1305 | — | 1000 | — | 1535 | 1332 |
| Mean | 1256 | 1602 | 1330 | 1389 | 1197 | 1695 | 926 | 1669 | 1480 | 1394 |
| Oil yield (Lbs/ac) | | | | | | | | | | |
| A3U7761 | 529 | 634 | 502 | — | 490 | 674 | — | 679 | 687 | 599 |
| Ames 26676 | 477 | 597 | 460 | — | 458 | — | — | — | 602 | 518 |
| Mean | 465 | 560 | 464 | — | 414 | 618 | — | 649 | 579 | 535 |
| Oil content (%) | | | | | | | | | | |
| A3U7761 | 37.12 | 37.1 | 35.28 | — | 34.35 | 36.16 | — | 39.03 | 39.59 | 36.94 |
| Ames 26676 | 37.04 | 36.8 | 35.04 | 34.24 | — | — | — | — | 38.81 | 36.38 |
| Mean | 36.90 | 35.75 | 34.89 | — | 33.84 | 36.21 | — | 38.64 | 38.63 | 36.41 |
| Seed weight (g/1000) | | | | | | | | | | |
| A3U7761 | 1.13 | 1.05 | 1.07 | 1.10 | 1.16 | 1.25 | 0.86 | 1.19 | 1.39 | 1.13 |
| Ames 26676 | 1.14 | 1.10 | 1.09 | 0.95 | 1.13 | — | 0.72 | — | 1.35 | 1.07 |
| Mean | 1.04 | 0.99 | 1.10 | 0.95 | 1.08 | 1.19 | 0.74 | 1.15 | 1.33 | 1.06 |
| Alpha-linolenic acid (%) | | | | | | | | | | |
| A3U7761 | — | 33.0 | 32.28 | — | — | 35.74 | — | 37.48 | — | 34.61 |
| Ames 26676 | — | 31.1 | 30.98 | — | — | — | — | — | — | 31.05 |
| Mean | — | 32.0 | 31.41 | — | — | 34.47 | — | 36.48 | — | 33.59 |

A modified bulk-pedigree selection scheme was used for the development of SO-100 (Table 11). A cross between accession "A3U7761" and accession "Ames 26676" was made in a field nursery in Kalispell, Mont. in the spring of 2006. During the winter of 2006/2007, the seed of this hybrid was advanced to the F2 generation at a nursery in Yuma, Ariz., and in the spring of 2007, seed of this F2 population was grown in a selection nursery near Bozeman, Mont. in duplicated plots (100 ft$^2$ each).

At maturity, 30 individual plants were selected and harvested from this population. Selection focused on early maturity, medium plant height, increased branch and pod number, and good overall appearance. A sample of seed from each of these F3 families was collected and bulked, and during the winter season of 2007/2008, this bulked seed was planted in a winter nursery near Yuma, Ariz. in duplicated plots (100 ft$^2$ each).

At maturity, an unrecorded number of individual plants were selected and harvested from this population using the criteria described above and a random portion of seed from each plant was collected and bulked. During the spring season of 2008, the bulked F4 seed from this population was planted in duplicated plots (100 ft$^2$ each) in a selection nursery in Bozeman, Mont.

At maturity, 20 individual plants were selected from this population using the same criteria as before. Seed from each of these individual F5 plants was planted in single rows in a nursery near Amsterdam, Mont. in the spring of 2009.

At maturity, one line was selected based on the same selection criteria stated before. Seed of the selected line, C09-BZ-SB6_229_8, was purified and increased during the spring of 2010 in an isolated strip plot near Amsterdam, Mont.

TABLE 11

Breeding method used in the development of SO-100.

| Generation | Activity | Season | Location |
|---|---|---|---|
| F1 | Crosses | Spring 2006 | Kalispell, MT |
| F2 | Seed advance | Winter 2006/2007 | Yuma, AZ |
| F3 | Sample of seed from each F2 plant bulked and planted in duplicated plots in a spring nursery. Single plant selections (30 individual plants selected). Selection criteria included early maturity, short plant stature, increased branching, increased pod number, good overall appearance. | Spring 2007 | Bozeman, MT |
| F4 | Sample of seed from each F3 line bulked and planted in a winter nursery. Single plant selections (unrecorded number for individual plants selected), selection criteria included early maturity, short stature, increased branching, increased pod number, overall good appearance. | Winter 2007/2008 | Yuma, AZ |
| F5 | Sample of seed from each F4 line bulked and planted in duplicated plots in a spring nursery. Single plant selections (20 individual plants selected), selection criteria included early maturity, short stature, increased branching, increased pod number, overall good appearance. | Spring 2008 | Bozeman, MT |
| F6 | Sample of seed from selected individual plants from the F5 population planted in single-row plots in a nursery. Experimental line C09-BZ-SB6_229_8 (S0-100) was selected. Selection criteria included early maturity, short plant stature, increased branching, increased pod number, good overall appearance. | Spring 2009 | Amsterdam, MT |
| F7 | Seed increase and seed purification in isolation field. | Spring 2010 | Amsterdam, MT |
| F7 | Multi-location yield evaluation trials. Seed oil quality evaluations. | Spring 2010 | Bozeman, MT; Carrington, ND; Dusty, WA, Havre, MT; Huntley, MT; Lingle, WY Pendleton, OR Saskatoon, SK, CAN |
| F8 | Multi-location yield evaluation trials. Seed oil quality evaluations. | Spring 2011 | Amsterdam, MT Carrington, ND; Havre, MT; Huntley, MT; Pendleton, OR |

TABLE 11-continued

Breeding method used in the development of SO-100.

| Generation | Activity | Season | Location |
|---|---|---|---|
| F9 | Multi-location yield evaluation trials. Seed oil quality evaluations. | Spring 2019 | Huntley, MT; Moccasin, MT; Pendleton, OR; Scottsbluff, NE. |

Example 5—Characteristics of *Camelina Sativa* (L.) Variety so-100

Breeder seed of variety SO-100 and other plant materials, including SO-50 (a patented variety used as a control variety to determine the relative value of SO-100 (see U.S. Pat. No. 8,319,021)), was grown in a growth chamber in Great Falls, Mont. Throughout the life cycle, the growth chamber was kept at an average temperature of 65° F. (range of 61° F. to 72° F.), with a photoperiod of 16 h light and 8 h dark. Light intensity was adjusted to 250 μmol/m$^2$/s at bench height and to 350 μmol/m$^2$/s at the top of the canopy. Relative humidity was set to approximately 65%.

Seeds of these varieties were planted in single pots 6 inches in diameter and 5.75 inches in height at a rate of 2 seeds per pot in a Sunshine Mix #4 grow soil media substrate. To accommodate for room for other plant materials, SO-100 was planted in 17 pots and SO-50 in 9 pots. Once the seedlings reached the 3-leaf stage, they were thinned to only one seedling per pot. Plants were fertilized with a 20-20-20 mix, providing an equivalent of 350 lb. of nitrogen per acre. Plants were watered daily as needed by ensuring the soil was approximately at water holding capacity. The data collected from these plants included plant height, raceme number, main raceme length (cm), inflorescence height (cm), pod number, total pod weight (g), seeds per pod, seed number, 1000-seed weight (g), and seed yield per plant (g). Plants were harvested by hand once they reached the maturity stage.

Under controlled conditions, SO-100 reached an average plant height of 86 cm, which was 9 cm taller than the average plant height of SO-50. Although their number of racemes were comparable, SO-100 developed a more prominent inflorescence structure than SO-50, with a longer main-raceme length (48 cm vs. 40 cm) and an increased inflorescence height (90 cm vs. 81 cm). Pod development was significantly enhanced in SO-100 compared to SO-50 (pod number 924 vs. 695, total pod weight 13.3 g vs. 12.5 g). Although the number of seeds per pod were slightly lower in SO-100 compared to SO-50 (8 vs. 10), the number of seeds per plant was significantly higher in SO-100 (7221 vs. 7075), constituting the main, unique attribute of variety SO-100. One-thousand seed weight and seed yield per plant were comparable attributes between these varieties (1.04 g vs. 1.06 g and 7.3 vs. 7.4 g, respectively).

TABLE 12

Yield component attributes of variety SO-100

| Plant trait | Mean | Max | Min | SD |
|---|---|---|---|---|
| SO-100 | | | | |
| Plant Height (cm) | 86 | 103 | 72 | 8.2 |
| Raceme Number | 17 | 24 | 13 | 3.0 |
| Main Raceme Length (cm) | 48 | 62 | 38 | 7.4 |
| Inflorescence Height (cm) | 90 | 103 | 78 | 7.2 |
| Pod Number | 924 | 1405 | 533 | 249.4 |
| Total pod weight (g) | 13.3 | 19.1 | 8.8 | 3.1 |
| Seeds Per Pod | 8 | 11 | 5 | 1.7 |
| Seed Number | 7221 | 10432 | 4136 | 1822.3 |
| 1000-Seed Weight (g) | 1.04 | 1.36 | 0.86 | 0.15 |
| Seed Yield Per Plant (g) | 7.3 | 10.1 | 5.4 | 1.4 |
| SO-50 | | | | |
| Plant Height (cm) | 77 | 83 | 70 | 5.5 |
| Raceme Number | 18 | 21 | 13 | 2.4 |
| Main Raceme Length (cm) | 40 | 51 | 34 | 5.3 |
| Inflorescence Height (cm) | 81 | 90 | 70 | 5.2 |
| Pod Number | 695 | 897 | 518 | 108.2 |
| Total pod weight (g) | 12.5 | 16.8 | 9.0 | 2.3 |
| Seeds Per Pod | 10 | 12 | 8 | 1.1 |
| Seed Number | 7075 | 9892 | 4600 | 1656.9 |
| 1000-Seed Weight (g) | 1.06 | 1.28 | 0.89 | 0.13 |
| Seed Yield Per Plant (g) | 7.4 | 9.2 | 4.8 | 1.4 |

All publications, patents, and patent publications cited are incorporated by reference herein in their entirety for all purposes. Also incorporated by reference herein are nucleic acid sequences and polypeptide sequences deposited into the GenBank, which are cited in this specification.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Anonymous. 2009. 14 Airlines sign landmark MOU for *Camelina*-based renewable jet fuel & green diesel, Dec. 15, 2009. Business Wire.

Berti, M. T. and A. A. Schneiter. 1993. Preliminary agronomic evaluation of new crops for North Dakota. p. 105-109. In: J. Janick and J. E. Simon (eds.), New crops. Wiley, New York.

Bouby, L. 1998. Two early finds of gold-of-pleasure (*Camelina* sp.) in middle Neolithic and Chacolithic sites in western France. Antiquity, 72: 391-398.

Brown et al. 1991. Tetrahedron, Vol. 47, Iss. 24, 3909-3914.

Budin, J. T., W. M. Breene and D. H. Putnam, 1995. Some compositional properties of *Camelina* (*Camelina sativa* (L.) Crantz) seeds and oils. Journal of the American Oil Chemists Society, 72: 309-315.

Eberhart, S. A., and W. A. Russell, 1966. Stability parameters for comparing varieties. Crop. Sci., 6: 36-40.

Finlay, K. W., and G. N. Wilkinson, 1963. The analysis of adaptation in a plant-breeding programme. Aust. J. Agr. Res., 14: 742-754.

Gugel, R. K. and K. C. Falk. Agronomic and seed quality evaluation of *Camelina sativa* in western Canada. 2006. Canadian Journal of Plant Science, 86:1047-1058.

Schultze-Motel, J., 1979. Die Anbaugeschichte des Leindotters, *Camelina sativa* (L.) Crantz.

Pavlista and Baltensperger, 2007, Phenology of Oilseed Crops for Bio-Diesel in the High Plains.

Pilgeram et al., 2007, *Camelina sativa*, A Montana Omega-3 and Fuel Crop, Issues in new crops and new use. InL J. Janick and A Whipkey (eds.). ASHS Press, Alexandria, Va.

Public Law 110-140. Energy Independence and Security Act of 2007.

Putnam, D. H., J. T. Budin, L. A. Field, and W. M. Breene. 1993. *Camelina*: A promising low-input oilseed. p. 314-322. In J. Janick, and J. E. Simon (eds), New Crops, Exploration, Research and Commercialization, John Wiley and Sons, Inc. New York, USA.

Robinson, R. G. 1987. *Camelina*: a useful research crop and a potential oilseed crop. University of Minnesota Agric. Exp. Stn. Bull. 579-1987 (Item No. AD-SB-3275), pp. 1-12.

Shonnard, D. R., L. Williams; and T. N. Kalnesc. 2010. *Camelina*-Derived Jet Fuel and Diesel: Sustainable Advanced Biofuels. Environmental Progress & Sustainable Energy, 29:382-392.

Vollmann, J., A. Damboeck, A. Eckl, H. Schrems, and P. Ruckenbauer. 1996. Improvement of *Camelina saliva*, an underexploited oilseed. p. 357-362. In: J. Janick (ed.), Progress in new crops. ASHS Press, Alexandria, Va.

I claim:

1. A seed of *Camelina sativa* (L.) variety designated "SO-100," wherein a representative sample of seed of said variety has been deposited under ATCC Accession No. PTA-126938.

2. A *Camelina sativa* (L.) plant, or a part thereof, produced by growing the seed of claim 1.

3. A *Camelina sativa* (L.) plant, or a part thereof, having all the physiological and morphological characteristics of *Camelina sativa* (L.) variety "SO-100," wherein a representative sample of seed of said variety has been deposited under ATCC Accession No. PTA-126938.

4. A tissue culture of regenerable cells produced from the plant or plant part of claim 2.

5. The tissue culture of claim 4, wherein said cells of the tissue culture are produced from a plant part selected from the group consisting of embryos, meristematic cells, leaves, pollen, root, root tips, stems, anther, pistils, pods, flowers and seeds.

6. A *Camelina sativa* (L.) plant regenerated from the tissue culture of claim 5, said plant having the morphological and physiological characteristics of *Camelina sativa* (L.) variety "SO-100," wherein a representative sample of seed has been deposited under ATCC Accession No. PTA-126938.

7. A method for producing a *Camelina* seed comprising crossing a first parent *Camelina* plant with a second parent *Camelina* plant and harvesting the resultant hybrid bean seed, wherein said first parent *Camelina* plant or second parent *Camelina* plant is the *Camelina sativa* (L.) plant of claim 2.

8. A hybrid *Camelina* seed produced by the method of claim 7.

9. A method for producing an herbicide-resistant *Camelina* plant comprising transforming the *Camelina saliva* (L.) plant of claim 2 with a transgene that confers herbicide resistance to an herbicide selected from the group consisting of imidazolinone, sulfonylurea, glyphosate, glufosinate, L-phosphinothricin, triazine, and benzonitrile.

10. An herbicide resistant *Camelina* plant, or a part thereof, produced by the method of claim 9.

11. A method for producing an insect resistant *Camelina* plant comprising transforming the *Camelina saliva* (L.) plant of claim 2 with a transgene that confers insect resistance.

12. An insect resistant *Camelina* plant, or a part thereof, produced by the method of claim 11.

13. A method for producing a disease resistant *Camelina* plant comprising transforming the *Camelina sativa* (L.) plant of claim 2 with a transgene that confers disease resistance.

14. A disease resistant *Camelina* plant, or a part thereof, produced by the method of claim 13.

15. A method of introducing a desired trait into *Camelina sativa* (L.) variety "SO-100" comprising:
   (a) crossing a *Camelina saliva* (L.) variety "SO-100" plant grown from *Camelina saliva* (L.) variety "SO-100" seed, wherein a representative sample of seed has been deposited under ATCC Accession No. PTA-126938, with another *Camelina* plant that comprises a desired trait to produce F1 progeny plants;
   (b) selecting one or more progeny plants that have the desired trait to produce selected progeny plants;
   (c) crossing the selected progeny plants with the *Camelina saliva* (L.) variety "SO-100" plants to produce backcross progeny plants;
   (d) selecting for backcross progeny plants that have the desired trait and physiological and morphological characteristics of *Camelina saliva* (L.) variety "SO-100" to produce selected backcross progeny plants; and
   (e) repeating steps (c) and (d) three or more times in succession to produce selected fourth or higher backcross progeny plants that comprise the desired trait and the physiological and morphological characteristics of *Camelina saliva* (L.) variety "SO-100."

16. A *Camelina* plant produced by the method of claim 15, wherein the plant has the desired trait and otherwise all the physiological and morphological characteristics of *Camelina saliva* (L.) variety "SO-100."

17. A method for producing *Camelina saliva* (L.) variety "SO-100" seed comprising crossing a first parent *Camelina saliva* (L.) plant with a second parent *Camelina saliva* (L.) plant and harvesting the resultant *Camelina saliva* (L.) seed, wherein both said first and second *Camelina saliva* (L.) plants are the *Camelina saliva* (L.) plant of claim 4.

18. The *Camelina* plant of claim 16, wherein the desired trait is herbicide resistance and the resistance is conferred to an herbicide selected from the group consisting of imidazolinone, sulfonylurea, glyphosate, glufosinate, L-phosphinothricin, triazine, and benzonitrile.

19. The *Camelina* plant of claim 16, wherein the desired trait is insect resistance and the insect resistance is conferred by a transgene encoding a *Bacillus thuringiensis* endotoxin.

20. The *Camelina* plant of claim 16, wherein the desired trait is selected from the group consisting of insect resistance, disease resistance, water stress tolerance, heat tolerance, improved shelf life, and improved nutritional quality.

* * * * *